United States Patent [19]

Masilamani et al.

[11] 4,239,929
[45] Dec. 16, 1980

[54] AROMATIZATION OF DIENES IN THE LIQUID PHASE

[75] Inventors: Divakaran Masilamani, Morristown; Milorad M. Rogic, Whippany, both of N.J.

[73] Assignee: Allied Chemical Corporation, Morris Township, Morris County, N.J.

[21] Appl. No.: 956,756

[22] Filed: Nov. 1, 1978

[51] Int. Cl.³ .......................... C07C 5/20; C07C 15/10
[52] U.S. Cl. .................................. 585/442; 568/570; 568/573
[58] Field of Search .................. 260/668 R, 668 D; 585/432, 442

[56] References Cited

U.S. PATENT DOCUMENTS

| | | | |
|---|---|---|---|
| 2,126,817 | 8/1938 | Roseu | 585/330 |
| 2,720,550 | 10/1955 | Dauforth | 585/587 |
| 3,585,249 | 6/1971 | Cohen et al. | 585/442 |
| 3,585,250 | 6/1971 | Pasternak et al. | 585/442 |
| 3,590,090 | 6/1971 | Cohen et al. | 585/442 |

OTHER PUBLICATIONS

R. K. Haynes Australian J. Chem. 31, pp. 121-129, 131-138, 1978.
R. B. Bates et al. J. Org. Chem. 34, No. 9, pp. 2615-2617, 1969.
D. H. R. Barton et al., J. Chem. Soc., Perkins Trans, I pp. 2055-2065; 2065-2068, 1975.
Divakar Masilamani et al., Tetrahedron Letters, No. 40, pp. 3785-3788, 1978.

*Primary Examiner*—Veronica O'Keefe
*Attorney, Agent, or Firm*—Alan M. Doernberg; Robert A. Harman

[57] ABSTRACT

Alkyl cyclohexa-1,3-dienes are aromatized with sulfur dioxide and oxygen. Cyclohexa-1,4-dienes are aromatized with sulfur dioxide. Conjugated dienic hydrocarbons, including alkyl cyclohexa-1,3-dienes, are converted to beta-olefinic peroxides by sulfur dioxide and oxygen. The aromatization reactions are useful as part of the synthesis of selected aromatics from acyclic olefins. The beta-olefinic peroxides are useful intermediates in the production of 1,4-diols.

11 Claims, No Drawings

AROMATIZATION OF DIENES IN THE LIQUID PHASE

BACKGROUND OF THE INVENTION

The oxygenation of certain conjugated dienes to form peroxides is known. For example alpha-terpinene (1-methyl,4-isopropylcyclohexa-1,3-diene) has been converted to ascaridole under irradiation. Ergosterol acetate has been converted to a peroxide with irradiation and with various Lewis acids.

Sulfur dioxide is a known Lewis acid and solvent for low temperature reactions. Sulfur dioxide has the disadvantage, however, of polymerizing many olefins to form polysulfones, which are unwanted by-products for many reactions including the ones described herein. In our copending application Ser. No. 862,313, filed Dec. 20, 1977, we described the use of sulfur dioxide to catalyze allylic isomerization or deuteration of certain monoolefins.

SUMMARY OF THE INVENTION

The present invention includes a method of producing aromatic compounds which comprises reacting in the liquid phase sulfur dioxide with a diene selected from alkyl cyclohexa-1,3-dienes of the formula

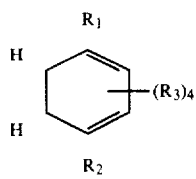

where $R_1$ is alkyl of 1–6 carbons, $R_2$ is hydrogen or alkyl of 1–6 carbons and $R_3$ is independently in each occurrence hydrogen or alkyl of 1–6 carbons, and cyclohexa-1,4-dienes, under conditions producing the corresponding aromatic compound. In the case of cyclohexa-1,3-dienes, these conditions include the presence of oxygen.

The present invention also includes a method of preparing a beta-olefinic peroxide which comprises reacting in the liquid phase at below about $-20°$ C. a conjugated dienic hydrocarbon with sulfur dioxide and oxygen under conditions producing the corresponding beta-olefinic peroxide. Temperatures below about $-50°$ C. are preferred to prevent the beta-olefinic peroxide from further reacting.

DETAILED DESCRIPTION OF THE INVENTION

One aspect of the present invention involves the preparation of aromatics from hexadienes in the presence of sulfur dioxide. It has been discovered that not all hexadienes will be aromatized by sulfur dioxide, but that certain conjugated (1,3) hexadienes can be aromatized by sulfur dioxide and oxygen and preferably also water, while many nonconjugated (1,4) hexadienes are quantitatively aromatized by sulfur dioxide alone. The aromatization of hexadienes is important in the synthesis of aromatics from acyclic olefins such as butadiene. Thus butadiene may be dimerized to vinyl cyclohexene and this compound isomerized to ethyl cyclohexa-1,3-diene or ethyl-cyclohexa-1,4-diene or mixtures thereof and these dienes aromatized according to the present invention to ethylbenzene.

Considering first the nonconjugated cyclohexadienes, it has been found that a variety of alkyl substituted and polyalkyl substituted cyclohexa-1,4-dienes, as well as cyclohexa-1,4-diene itself, react with sulfur dioxide at room temperature to form the corresponding aromatic compound, elemental sulfur and water. Thus cyclohexa-1,4-diene and sulfur dioxide produce benzene, sulfur and water at room temperature. Ethyl cyclohexa-1,4-diene reacts with sulfur dioxide to quantitatively produce ethyl benzene, sulfur and water.

Most conjugated cyclohexadienes do not readily produce aromatics when reacted with sulfur dioxide, but instead generally either produce polymers which are believed to be polysulfones or produce sulfolene compounds. It has been found, however, that certain alkyl substituted cyclohexa-1,3-dienes can be aromatized by sulfur dioxide and oxygen. Thus alpha-terpinene (1-isopropyl, 4-methyl cyclohexa-1,3-diene) reacts at room temperature with sulfur dioxide and oxygen to form para-cymene (1-isopropyl, 4-methyl benzene), sulfuric acid. It is expected that under proper conditions 1-ethyl cyclohexa-1,3-diene will react with sulfur dioxide and oxygen to form ethyl benzene and sulfuric acid. Under many conditions tested thus far, however, 1-ethyl cyclohexa-1,3-diene is polymerized by sulfur dioxide.

Suitable cyclohexa-1,4-dienes for aromatization include those of the formula

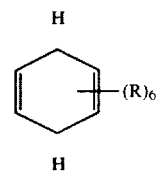

where R is independently at each occurrence hydrogen or alkyl of 1–6 carbons. Preferably, R is hydrogen in at least 5 occurrences. More preferably R is hydrogen in 5 occurrences and methyl, ethyl, isopropyl or butyl in the 6th occurrence.

Suitable alkyl cyclohexa-1,3-dienes for aromatization are of the formula

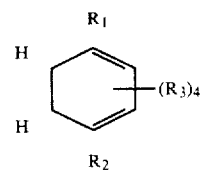

where $R_1$ is alkyl of 1–6 carbons, $R_2$ is hydrogen or alkyl of 1–6 carbons and $R_3$ is independently at each occurrence hydrogen or alkyl of 1–6 carbons. Preferably $R_3$ is hydrogen in all occurrences. Preferably $R_1$ is methyl, ethyl, isopropyl or butyl. Preferably $R_2$ is hydrogen, methyl, ethyl, isopropyl or butyl.

For aromatization of cyclohexa-1,4-dienes, individual reaction conditions are not critical, with essentially quantitative reaction occurring when sulfur dioxide is added to the diene at room temperature under laboratory lighting. Temperatures of about $-70°$ C. to $50°$ C. are preferred and, if sulfur dioxide is not dissolved in a less volatile solvent, then autogenous pressure is sometimes necessary.

Temperature is somewhat critical for aromatization of alkyl cyclohexa-1,3-dienes, with greater than about −50° C. being required to produce any aromatization and at least about −20° C. being preferred. A preferred range is about −20° C. to about 40° C. At temperatures lower than these, the reaction will stop at the endoperoxide as described below. If the sulfur dioxide is not dissolved in a less volatile solvent, then autogenous pressure is sometimes required.

For either reaction, sulfur dioxide is preferably present in excess, although an equimolar amount of diene and sulfur dioxide is apparently stoichiometric for the nonconjugated diene and a two to one ratio of sulfur dioxide to diene is apparently stoichiometric for the conjugated diene. For conjugated diene, oxygen is consumed at a rate of one mole of oxygen per mole of cyclohexa-1,3-diene, although excess oxygen may be used. Water is preferably present when the cyclohexa-1,3-diene is aromatized.

The present invention also includes the formation of beta-olefinic peroxides from conjugated dienes. Considering for example certain cyclohexa-1,3-dienes such as alpha terpinene, sulfur dioxide and oxygen will convert them under proper conditions to the corresponding 1,4-endoperoxy cyclohexa-2-ene such as ascaredol:

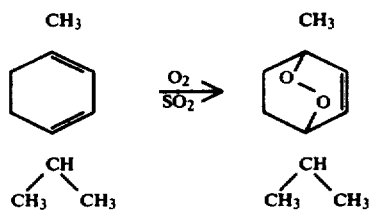

This reaction is also of interest with respect to acyclic dienes such as butadiene:

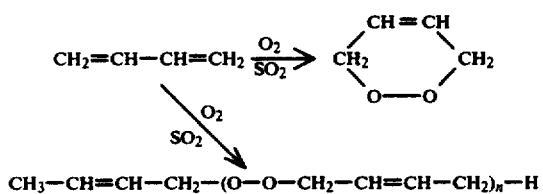

In experiments conducted thus far, the polymerization of butadiene has prevented desired reaction from being observed.

The reaction also occurs in polycyclic dienes such as ergosterol acetate as follows:

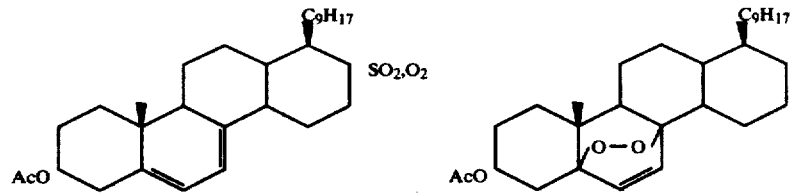

It has been discovered that, if the peroxide is the desired product, conditions must be carefully controlled to prevent further reaction with sulfur dioxide. In the case of alkyl cyclohexa-1,3-dienes, permitting the temperture to reach or exceed about −20° C. will cause all of the peroxide to aromatize. In the case of ergosterol acetate, similar conditions will lead to the formation of a triene (the location of all double bonds not having been established). In both cases, temperatures are preferably maintained at about −50° C. or below to prevent any loss of peroxide, with the preferred reaction temperature being between about −70° C. and about −50° C. In the less preferred range of −50° C. to −20° C., some of the peroxide will further react.

EXAMPLE 1

Preparation of Endoperoxide From -Terpinene

Sixty milliliters of sulfur dioxide were condensed into a 4-neck 250 ml flask provided with a magnetic stirrer, a dry-ice/acetone bath, Dewar condensers cooled by dry-ice/acetone and attached to an oxygen gas burette.

Sulfur dioxide was cooled to −70° C. and the flask was purged several times with oxygen. 0.83 gm (0–006 mole) of p-mentha-1,3-diene (α-terpinene) was added through a rubber septum by means of a syringe and the oxygen uptake was observed while maintaining the temperature at −70±1° C. About 130 ml of oxygen at ambient temperature were absorbed in 3½ hrs. (expected uptake 136 ml.)

The original pale yellow color of the reaction mixture somewhat intensified in 3½ hrs. The final reaction product was poured into 250 ml of pentane and sulfur dioxide was removed on a rotary evaporator using a vacuum pump at −50° to −60° C.

The pentane solution was washed successively with 3×100 milliliters of water, 2×100 milliliters of saturated sodium bicarbonate solution and 2×100 milliliters of water. It was dried over anhydrous sodium sulfate. Pentane was again removed on a rotary evaporator at room temperature to yield 0.75 gms of p-mentha-1,3-diene endoperoxide ("ascaridole") upon which a yield of 73% was computed. Analysis of the product by nmr and gas-liquid chromotography showed that the endoperoxide was 98=1% pure. The remainder was p-cymene. A summary of this Example is shown in Table I.

EXAMPLES 2–5

Example 1 was repeated with the quantities and when the conditions shown in Table I. With complete conversion of α-terpinene, the yield (without compensating for impurities) and purity were determined as shown in Table I. All examples were run under laboratory lighting except Example 5.

TABLE I

| Example | Diene gm(M) | Solvent (ml) | Temp °C. | Time hrs. | $O_2$ ml | Yield & | Purity % |
|---|---|---|---|---|---|---|---|
| 1 | .83 | $SO_2$ | −70 | 3.5 | 130 | 73 | 98 |

TABLE I-continued

| Example | Diene gm(M) | Solvent (ml) | Temp °C. | Time hrs. | O$_2$ ml | Yield % | Purity % |
|---|---|---|---|---|---|---|---|
| 2 | (0.006) .88 | (60) SO$_2$ (60) | ±1 −49 | 2.25 | 128 | 78 | 99 |
| 3 | (.0065) .86 | CH$_2$Cl$_2$ (60) SO$_2$ (1.5) | −35 ±5 | 3 | 126 | 94 | 52 |
| 4 | (.0063) 2.3 | CH$_2$Cl$_2$ (200) SO$_2$ (2) | −20 | 4 | NM | 50 | 50 |
| *5 | 0.84 (.0062) | SO$_2$ (60) | −72 ±1 | 4.25 | 109 | 89 | 99 |

NM = Not measured.
*Example 5 conducted in the dark.

EXAMPLE 6

Preparation of Endoperoxide From Ergosteryl Acetate 0.6 gm (0.00137 mole) of ergosteryl acetate was dissolved in 25 ml of sulfur dioxide in a 100 ml 4-neck flask provided with a magnetic stirrer, dry-ice/acetone bath, Dewar condensers cooled by dry-ice/acetone and attached to an oxygen gas burette.

The solution was cooled to −70° and the flask was purged several times with oxygen. The entire set up was exposed to light from a 500 watt tungsten lamp 3 feet away.

The expected amount of oxygen (30 ml) was absorbed in 2 hrs. 25 ml of CH$_2$Cl$_2$ was added and the SO$_2$ was removed at −50° to −60° at the rotary evaporator using a vacuum pump.

The pale yellow solid residue that remained weighed 0.56 g (90% yield). The nmr of the solid as identical in all respect to the authentic sample of ergosteryl acetate endoperoxide.

COMPARATIVE EXAMPLES 7–9

Example 7 was repeated at −70° C. in the dark and twice a room temperature under laboratory lighting with a small amount of SO$_2$ in methylene chloride as the solvent. In the dark, no conversion or oxygen uptake was detected after four hours. In both room temperature experiments, the conversion was complete and the yields of a product high; however, nmr analysis showed the product to be a triene rather than the desired endoperoxide.

EXAMPLES 10–12

Attempts were made to repeat Example 6 using as starting materials butadiene, 1,1'-bicydohexenyl and 1,3-cyclopentadiene. The only products detected were, respectively, polysulfones, a sulfolene and a polymer. It is believed, however, that such starting materials will, when run under proper conditions, product peroxides.

EXAMPLE 13

Aromatization of α-Terpinene 0.83 gm (0.006 mole) of p-mentha-1,3-diene (α-terpinene) dissolved in 60 ml of CH$_2$Cl$_2$ was taken in a 100 ml pressure bottle provided with a magnetic stirrer. 1.5 ml of sulfur dioxide was condensed and the bottle was connected to an oxygen gas burrette. The reaction mixture was stirred at room temperature. 128 milliliters of oxygen was absorbed in 1 hr. (Expected 135 milliliters).

The product was diluted with 50 milliliters of CH$_2$Cl$_2$ and washed with water. The water layer was acidic and formed barium sulfate when treated with barium chloride solution.

The CH$_2$Cl$_2$ layer was washed with 100 ml of saturated sodium bicarbonate solution and 100 ml of water. It was dried over anhydrous sodium sulfate and concentrated to yield one gram of brownish product. nmr and glc analysis showed 95% p-cymene and 5% polymeric materials. The results are summarized in Table III.

EXAMPLES 14–17

Example 13 was repeated under the conditions shown in Table II. Laboratory lighting was present in all examples except Example 15. All Examples were conducted at room temperatures. The conversion was 100% in all Examples.

TABLE II

| Example | Solvent (ml) | Time | O$_2$ ml | Yield | p-Cymene | polymer |
|---|---|---|---|---|---|---|
| 13 | CH$_2$Cl$_2$ (60) SO$_2$ (1.5) | 1 hr. | 128 | 99 | 95 | 5 |
| *14 | CH$_2$Cl$_1$ (60) SO$_2$ (1.5) | overnight | 116 | 85 | 90 | 4 |
| 15 | CH$_2$Cl$_2$ (60) SO$_2$ (1.5) H$_2$O (1.0) | 4 hrs. | 130 | 100 | 90 | 10 |
| 16 | SO$_2$ (60) H$_2$O (4) | 5 days | NM | 87 | 87 | 13 |
| 17 | SO$_2$ (60) | 2 days | NM | 100 | 10 | 90 |

NM = Not measured.
*Example 15 conducted in the dark.

EXAMPLE 18

Sixty milliliters of sulfur dioxide were condensed in a 100 milliliter pressure bottle cooled at −15° C. 3.2 g (0.0235 M) of 1-Methyl-4-isopropylcyclohexa-1,4-diene (γ-terpinene) was added by means of syringe. The bottle was stoppered and stirred magnetically at room temperature for 80 hours. Yellow sulfur was deposited on the sides of the bottle.

SO$_2$ was allowed to escape. Sulfur was filtered off. 50 ml of CH$_2$Cl$_2$ was then added and water formed in the reaction was removed by anhydrous sodium sulfate.

The dried CH₂Cl₂ layer was filtered and concentrated to yield 2.4–2.7 gm of p-cymene (66–85% yield).

EXAMPLES 19–20

Example 18 was repeated in smaller scale with 2 grams of γ-terpinene in 50 ml SO₂ and with 0.071 grams of γ-terpinene in 0.86 ml SO₂, with complete conversion after 80 and 24 hours, respectively to p-cymene.

EXAMPLE 21

Example 18 was repeated using 0.2 gram 1-ethyl-cyclohexa-1,4-diene and 1.1 ml SO₂. After 24 hours, complete conversion to ethylbenzene was observed.

EXAMPLE 22

Example 18 was repeated with 0.2 gram cyclohexa-1,4-diene and 0.7 ml SO₂. After 28 days, the conversion was only 85%, but the product was essentially all benzene.

EXAMPLE 23

A mixture of 3-ethylidenecyclohexene (96%), 1-ethylcyclohexa-1,3-diene (3–4%) and trace amounts of 1-ethylcyclohexa-1,5-diene and 1-ethylcyclohexa-1,4-diene was prepared from 4-vinylcyclohexene by a procedure similar to that reported by R. B. Bates et al. in *J. Org. Chem.*, vol. 34, pp. 2615–2617 (1969). 4 grams of potassium t-butoxide were dissolved in 50 milliliters of dry dimethylsulfoxide and 5 milliliters (4.2 grams) of 4-vinylcyclohexene was added. The solution turned dark and was heated overnight at 50° C. under a nitrogen atmosphere. The following morning, 50 milliliters of saturated sodium chloride solution were added, the product was extracted three times with 100 milliliters of ether and the ether extract was dried over anhydrous sodium sulfate and concentrated to yield 3.8 grams of brown liquid. Gas liquid chromatography analysis of the product using a 10 foot 10% carbowax column showed the product distribution indicated above.

Four grams (0.037 mole) of such a mixture of dienes were dissolved in 60 milliliters of methylene chloride in a pessure bottle provided with a magnetic stirrer. 5 milliliters of sulfur dioxide were condensed into the bottle and the mixture was stirred overnight while exposed to oxygen from a gas burette (about 40 milliliters oxygen was consumed).

The reaction mixture was treated with 40 milliliters methylene chloride and dried over anhydrous sodium sulfate and concentrated in a rotary evaporator to yield 3.8 grams (95%) of a product.

Gas liquid chromatography analysis on an ov-1 column (10%, 6-foot) showed about 5% ethylbenzene, 42% polymer and about 43% unreacted 3-ethylidenecyclohexane.

The results correspond to aromatization of essentially all of the cyclohexadiene components of the mixture according to the method of the present invention. The initial starting material 4-vinylcyclohexene can be prepared from butadiene. Techniques have been proposed to increase the cyclohexadiene content of the mixture first formed.

What is claimed is:

1. A method of producing aromatic compounds which comprises reacting in the liquid phase sulfur dioxide with a diene selected from the group consisting of alkyl cyclo-hexa-1,3-dienes of the formula:

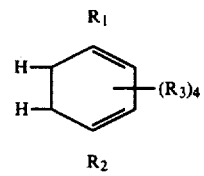

where R₁ is alkyl of 1–6 carbons, R₂ is hydrogen or alkyl of 1–6 carbons and R₃ is independently at each occurrence hydrogen or alkyl of 1–6 carbons, and cyclohexa-1,4-dienes, under conditions producing the corresponding aromatic compound, including, when the diene is an alkyl cyclohexa-1,3-diene, the presence of oxygen.

2. The method of claim 1 wherein the diene is a cyclohexa-1,4-diene of the formula:

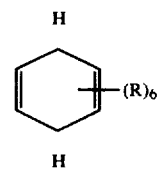

where R is independently at each occurrence hydrogen or alkyl of 1–6 carbons.

3. The method of claim 2 wherein R is hydrogen in at least five occurrences.

4. The method of claim 3 wherein R is hydrogen in five occurrences and hydrogen, methyl, ethyl, isopropyl or butyl in the sixth occurrent.

5. The method of claim 4 wherein R is hydrogen in all six occurrences.

6. The method of claim 4 wherein R is ethyl in the sixth occurrence.

7. The method of claim 1 wherein the diene is an alkyl cyclohexa-1,3-diene and the reaction conditions include a temperature of greater than about −50° C.

8. The method of claim 7 wherein the temperature is at least about −20° C.

9. The method of claim 7 wherein R₃ is hydrogen in all occurrences.

10. The method of claim 9 wherein R₁ and R₂ are each independently methyl, ethyl, isopropyl or butyl.

11. The method of claim 9 wherein R₁ is methyl, ethyl, isopropyl or butyl and R₂ is hydrogen.

* * * * *